(12) United States Patent
Weigel et al.

(10) Patent No.: US 7,670,986 B2
(45) Date of Patent: Mar. 2, 2010

(54) MANGANESE DIOXIDE CATALYST FOR THE HYDROLYSIS OF CARBONITRILES

(75) Inventors: Horst Weigel, Rodenbach (DE); Axel Ronneburg, Erlensee (DE); Christoph Weckbecker, Gründau-Lieblos (DE)

(73) Assignee: Degussa AG, Duesseldorf (DE)

( * ) Notice: Subject to any disclaimer, the term of this patent is extended or adjusted under 35 U.S.C. 154(b) by 201 days.

(21) Appl. No.: 11/538,898

(22) Filed: Oct. 5, 2006

(65) Prior Publication Data

US 2007/0117980 A1    May 24, 2007

(30) Foreign Application Priority Data

Oct. 5, 2005    (DE)    ........................ 10 2005 047 597

(51) Int. Cl.
*B01J 23/32*    (2006.01)
*B01J 23/00*    (2006.01)
*B01J 23/10*    (2006.01)
*C07C 231/00*    (2006.01)
*C07C 61/00*    (2006.01)
*C07C 61/08*    (2006.01)

(52) U.S. Cl. ........................ 502/302; 502/324; 502/303; 502/304; 502/344; 564/124; 562/400

(58) Field of Classification Search ......... 502/302–304, 502/324, 344; 564/124; 562/400
See application file for complete search history.

(56) References Cited

U.S. PATENT DOCUMENTS

| 4,018,829 | A |   | 4/1977 | Gruber et al. |
| 4,290,925 | A |   | 9/1981 | Mein et al. |
| 5,276,185 | A |   | 1/1994 | Karasawa et al. |
| 7,329,627 | B2 | * | 2/2008 | Wanninger et al. .......... 502/304 |
| 2004/0151647 | A1 | * | 8/2004 | Wanninger et al. .......... 423/247 |

FOREIGN PATENT DOCUMENTS

| DE | 1 593 320 |    | 10/1971 |
| EP | 0 412 310 | A1 | 2/1991 |
| EP | 0 597 298 | A1 | 5/1994 |
| EP | 0 731 079 | A2 | 9/1996 |
| FR | 2 750 987 | A1 | 1/1998 |
| JP | 09-104665 |    | 4/1997 |
| WO | WO97/19891 | A1 * | 6/1997 |

OTHER PUBLICATIONS

Abecassis-Wolfovich et al., "Cerium incorporated ordered manganse oxide OMS-2 materials: Improved catalysts for wet oxidation of phenol compounds," Applied Catalysis B: Enviornmental 59 (2005) 91-98.*
Jothiramalingam et al., "Preparation, characterization and catalytic properties of cerium incorporated porous manganese oxide OMS-2 catalysts," Catalysis Communications 6 (2005) 41-45.*
Hussain et al., "Enhancing the stability of Mn—Ce—O WETOX catalysts using potassium," Applied Catalysis B: Enviornmental 34 (2001) 1-9.*
Teraoka et al. "Synthesis of La—K—Mn—O perovskite-type oxides and their catalytic property for simultaneous removal of NOx and diesel soot particulates," Applied Catalysis B: Enviornmental 34 (2001) 73-78.*
Hussain et al. "Novel K-Doped Mn—Ce—O Wet Oxidation Catalysts with Enhanced Stability," Journal of Catalysis 201, 153-157 (2001).*
Santiago et al. "Kinetic and wet oxidation of phenol catalyzed by non-promoted and potassium-promoted manganese/cerium oxide," Journal of Hazardous Materials B 138 (2006) 325-330, Available online: Jul. 15, 2006.*

* cited by examiner

*Primary Examiner*—Steven Bos
*Assistant Examiner*—Anthony J Zimmer
(74) *Attorney, Agent, or Firm*—Smith Gambrell & Russell LLP

(57)    ABSTRACT

A manganese dioxide catalyst for hydrolysing organic nitrites which bear readily oxidizable groups such as thiol or thioether groups to the corresponding carboxamides, and to a process for preparing the catalyst and to its use for hydrolysing organic nitrites.

29 Claims, No Drawings

_US 7,670,986 B2_

MANGANESE DIOXIDE CATALYST FOR THE HYDROLYSIS OF CARBONITRILES

REFERENCE TO A RELATED APPLICATION

This application claims the benefit of applicants' German priority application 102005047597.3 filed Oct. 5, 2005, which is relied on herein.

INTRODUCTION AND BACKGROUND

The invention relates to a novel manganese dioxide catalyst which can be used for the hydrolysis of organic nitriles to the corresponding carboxamides, and to a process for preparing the catalyst. The invention also relates to a catalytic process for hydrolysing organic nitriles to the corresponding carboxamides with the aid of the catalyst.

The invention relates in particular to a catalytic process for hydrolysing 2-hydroxy-4-methylthiobutyronitrile to 2-hydroxy-4-methylthiobutyramide, a valuable intermediate in the preparation of 2-hydroxy-4-methylthiobutyric acid, the hydroxy analogue of methionine (MHA), and salts thereof. These substances find use as an animal feed additive, in particular in poultry breeding. These methionine-like compounds can replace methionine and significantly improve the utilization of proteins in the feed.

The hydrolysis of 2-hydroxycarbonitriles (cyano-hydrins) is a special case of nitrile hydrolysis. It is not possible to use any of the known processes for hydrolysing nitrites, in which strong bases may be used, because a back reaction of the cyanohydrin to aldehyde and hydrogen cyanide proceeds under these reaction conditions.

The 2-hydroxy-4-methylthiobutyronitrile can also be hydrolysed with highly concentrated mineral acids, preferably with sulphuric acid, in a virtually equimolar amount. In the first reaction step, the amide of the substituted butyric acid forms. An industrially readily realizable separation of 2-hydroxy-4-methylthiobutyramide and sulphuric acid, with the aim of being able to reuse the sulphuric acid, is, however, not known. Only after the hydrolysis of the amide to the hydroxycarboxylic acid is the mineral acid removed as ammonium hydrogensulphate, and worked up back to sulphuric acid in an additional, expensive process step.

It is also known that manganese dioxide catalyses the hydrolysis reaction of carbonitriles to amides, as described, for example, in DE 1593320.

As a result of the incorporation of manganese of other valence states into the crystal lattice, the stoichiometric composition of natural and synthetic manganese dioxide is in the range between $MnO_{1.7}$ and $MnO_{2.0}$. Extraneous ions such as sodium, potassium may be present in the crystals. Manganese dioxide exists in several allotropic modifications. They differ greatly in their behaviour as a catalyst. The crystallinity is at its most marked in pyrolysite (beta-manganese dioxide), the most stable modification. This form is catalytically inactive. The crystallinity is less marked in the further modifications and extends up to an amorphous product, ramsdellite. It is possible to assign the modifications by x-ray diffraction. Some of the chemically and catalytically active forms of manganese dioxide are hydrated and additionally contain hydroxyl groups.

Numerous patents describe catalytic processes for hydrolysing carbonitriles, especially 2-hydroxynitriles (cyanohydrins), with manganese dioxide. These processes are highly suitable, for example, for hydrolysing acetone cyanohydrin, as shown in U.S. Pat. No. 4,018,829, with which yields of over 90% are achieved in the hydrolysis of acetone cyanohydrin to 2-hydroxybutyramide with the aid of manganese dioxide.

The catalytically active modifications of manganese dioxide are, however, also active as oxidizing agents, which significantly restricts their use in the hydrolysis of thioether- or thiol-substituted nitrites, caused by their easy oxidizability. This reduces tetravalent manganese partly to trivalent manganese, and correspondingly oxidizes the sulphur.

DE 1593320 describes a process for hydrolysing nitrites to amides with the aid of manganese dioxide, in which yields up to over 90% were achieved with aliphatic nitrites. Only 8% yield of amide was achieved with thiodipropionitrile, which makes it clear that conventional manganese dioxide is hardly suitable as a catalyst in the presence of easily oxidizable thioether groups.

EP 0 597 298 describes a partial reduction of manganese dioxide by a pretreatment with reducing agents such as alcohol in order to improve the catalyst properties, in particular to suppress oxamide formation there. With increasing proportion of trivalent manganese oxide, however, the activity of the catalyst declines.

The oxidizing action of manganese dioxide is generally undesired in the hydrolysis of nitrites which bear easily oxidizable groups such as thiol or thioether groups. In particular, the S-oxidization is undesired in the hydrolysis of 2-hydroxy-4-methylthiobutyronitrile to 2-hydroxy-4-methylthiobutyramide, an important intermediate in the preparation of the animal feed additive 2-hydroxy-4-methylthiobutyric acid. Oxidation of the sulphur forms the sulphoxide and this ultimately reduces the yield of 2-hydroxy-4-methylthiobutyramide. This by-product formed by oxidation cannot be removed without a considerable level of cost and inconvenience and then leads to a contaminated end product which can no longer be used directly as an animal feed additive.

The reduction of the catalyst which is associated with the oxidization of the sulphur also shortens its lifetime, which, in an industrial process, leads to economic disadvantages, such as increased catalyst consumption and regeneration complexity with corresponding costs.

The patent JP 09104665 describes the preparation of active δ-manganese dioxide and defines its activity via the parameter of surface area. The hydrolysis of 2-hydroxy-4-methylthiobutyronitrile with full conversion is also described with this catalyst. There is no discussion whatsoever of the formation of sulphoxide in this publication on the part of the applicant. By virtue of application of the conditions specified there, it was, however, found that, during the reaction, the sulphoxide of 2-hydroxy-4-methylthiobutyronitrile is formed up to more than 4% in a selectivity of at least 1.6% (comparative example, Example 11), which is highly disadvantageous. Moreover, the nitrile conversion was only 96.1%, the amide yield 79.8% in continuous mode.

The same applicant describes, in the patent EP 0 731 079, a process for preparing carboxylic acids by hydrolysing cyanohydrin with the aid of manganese dioxide and subsequent hydrolysis of the amide formed with alkali to give the salt of the carboxylic acid. The electrodialysis then separates the carboxylic acid and sodium hydroxide solution from one another. In Example 3, in a column reactor with δ-manganese dioxide (amorphous) not described in more detail, the formation of MHA amide at 50° C. by hydrolysis of 2-hydroxy-4-methylthio-butyronitrile with a nitrile conversion of 100% is reported at an MHA amide yield of even 100%. It was likewise impossible to confirm this result. Instead, it was found that, especially in a column reactor with high catalyst concentration, the oxidizing action of active manganese dioxide comes to bear. With simultaneous reduction of manganese4+, this leads to catalytically inactive Mn3+ and to increased formation of the sulphoxide. The reworking of this example which is quite similar to JP 09104665 also shows that the sulphoxide of 2-hydroxy-4-methylthiobutyramide is formed with a selectivity of approx. 2% to more than 4%.

The patent FR 2 750 987 solves the problem of the oxidation of sulphur by coating silicon dioxide with manganese dioxide. However, the catalyst contains only 5 to 10% of active catalyst constituents. This must be balanced out by the use of a large amount of catalyst or by reaction times of 17 to 45 hours. For an industrial process, this procedure is disadvantageous.

SUMMARY OF THE INVENTION

Against the background of the disadvantages of the prior art, the inventors were faced with the object of providing a catalyst based on manganese dioxide which catalyzes the hydrolysis of carbonitriles which bear easily oxidizable groups such as thiol or thioether groups, especially corresponding hydroxynitriles to the corresponding amides. The oxidizing action of this catalyst should be sufficiently low that cyanohydrins which bear oxidizable functional groups such as thiol or thioether groups, i.e., for example, 2-hydroxy-4-methylthiobutyronitrile, should also be hydrolysable with it without significant S-oxidation. It was a further object to provide a suitable preparation process for the catalyst. It was a third object to provide a hydrolysis process which is readily performable industrially for carbonitriles, which is applicable to carbonitriles which bear easily oxidizable groups such as thiol or thioether groups, especially corresponding hydroxynitriles, with the proviso that the disadvantages of the known processes, especially the easy oxidation of sulphur, take place only to a reduced degree, if at all.

These objects, and also further objects which are not specified explicitly but which can immediately be derived or discerned from the connections discussed herein are achieved by a manganese dioxide catalyst which contains at least 52% by weight of manganese and additionally, at least one lanthanide compound; and, by a process for its preparation comprising reacting an alkali metal-containing manganese dioxide with at least one lanthanide salt in aqueous solution or suspension to obtain a solid, and removing the solid obtained, optionally washing and drying the solid and by a process for hydrolysing nitriles with the aid of the inventive catalyst; more particularly, a process for catalytic hydrolysis of carbonitriles of the general formula $R^1$—$CR^2R^3$—CN to form the corresponding carboxamides, where $R^1$, $R^2$ and $R^3$ may be the same or different and are each hydrogen, at least one S—R- or S—H-substituted hydrocarbon radical and $R^3$ is optionally a hydroxyl radical, where the particular hydrocarbon radical $R^1$, $R^2$, $R^3$ is a linear or optionally branched $C_1$- to $C_{10}$-alkyl radical, a $C_6$- to $C_{10}$-aryl radical, an O-, N- and/or S-containing $C_4$- to $C_8$-heteroaryl radical or a $C_7$- to $C_{12}$-aralkyl radical, and the R radical is a linear or optionally branched $C_1$- to $C_4$-alkyl, $C_6$- to $C_{10}$-aryl radical, an O-, N- and/or S-containing $C_4$- to $C_8$-heteroaryl radical or a $C_7$- to $C_{12}$-aralkyl radical, comprising carrying out the hydrolysis with the aid of a catalyst according to the invention. Appropriate embodiments and modifications of the invention catalyst, and of the process for its preparation and for its use, are protected in the subclaims herein.

The object was achieved in accordance with the invention by providing a manganese dioxide catalyst which contains at least 52% by weight of manganese, preferably at least 53% by weight of manganese, more preferably at least 55% by weight of manganese, and additionally at least one lanthanide compound. Surprisingly, it was found that the incorporation of small amounts of lanthanides into the manganese dioxide greatly reduced its undesired oxidizing action toward thioether or thiol groups without adversely affecting the catalytic action in the hydrolysis of carbonitriles.

In particular, the object is achieved by providing a catalyst of the type mentioned with the general formula:

where x is from 0.05 to 0.002, y is from 0.06 to 0.02 and z is from 1.7 to 2.0, Me is at least one element of lanthanides, M is an alkali metal (lithium, sodium, potassium, rubidium, caesium), and additional water of hydration may be present.

Elements particularly suitable in accordance with the invention from the group of the lanthanides are cerium and lanthanum. Particular preference is therefore given to catalysts in which Me is cerium and/or lanthanum.

The manganese dioxides modified in accordance with the invention contain, in addition to lanthanide, as extraneous ions, preferably lithium, sodium or potassium, most preferably potassium, which is important in an advantageous manner for the action in the catalysis of nitrile hydrolysis. Particular preference is thus also given to catalysts in which M is potassium.

The manganese dioxides modified in accordance with the invention have a specific surface area (BET) of 50 to 550 m²/g, preferably of 150 to 400 m²/g, most preferably of 200 to 300 m²/g, which is determined according to the test method DIN66131.

DETAILED DESCRIPTION OF INVENTION

The preparation of the catalyst is simple and can be effected, for example, by a treatment of commercially available active manganese dioxide with an aqueous solution of a salt of the lanthanides. The inventive process for preparing the catalyst is characterized in that alkali metal-containing manganese dioxide is reacted with at least one lanthanide salt in aqueous solution or suspension, and the solid obtained is removed, optionally washed and dried.

The process for preparing the catalyst is preferably performed in such a way that alkali metal-containing manganese dioxide is reacted with at least one lanthanide salt in aqueous solution or suspension in the suitable molar ratios, so as to obtain the resulting solid with the desired composition $MnMe_xM_yO_z$, and this is removed, optionally washed and then dried.

Active manganese dioxide is typically prepared by the reaction of potassium permanganate with sulphuric acid solution of manganese(II) sulphate, as reported, for example, in EP 412310 in Example 1. The salt of the lanthanides can also be added to the reaction solution actually in this reaction.

A preferred process for preparing the inventive catalyst consequently features, before and/or during the reaction of manganese dioxide with lanthanide salt, the direct preparation of the alkali metal-containing manganese dioxide from alkali metal permanganate, preferably potassium permanganate, and manganese(II) sulphate in sulphuric acid solution. This is particularly inexpensive and affords particularly active catalysts.

Alkali metal-containing manganese dioxide is preferably prepared from approx. 2 molar equivalents of alkali metal permanganate and approx. 3 molar equivalents of manganese (II) sulphate.

To prepare the catalyst, it is possible to use either inorganic or organic lanthanide salts, which further simplifies the catalyst preparation.

In the case of the inorganic lanthanide salts, preference is given to using the halides, nitrates, sulphates or phosphates, the phosphates being the most suitable.

In the case of the organic lanthanide salts, preference is given to using the carboxylic salts, especially the formates or acetates.

Since the inventive catalysts preferably contain cerium and/or lanthanum, they are prepared preferably by using the corresponding cerium and/or lanthanum salts.

The oxidizing action was the most reduced with trivalent salts of cerium; these are therefore used preferentially. It is also possible to use tetravalent salts of cerium for catalyst preparation.

Preference is therefore given to employing a process in which trivalent and/or tetravalent salts of cerium are used for catalyst preparation.

It has also been found that the most active catalysts are obtained when the manganese dioxide used is present in the crystal modification of α-manganese dioxide, especially in the case of use of commercial material.

A further significant aspect of the invention is the use of the inventive catalysts for the hydrolysis of nitriles.

The inventive catalysts also feature, in addition to the reduced sulphoxide formation in the hydrolysis of thioether-containing nitriles, simultaneously the achievement of further activation of the manganese dioxide catalyst used compared to the manganese dioxide catalysts prepared without lanthanide salt.

This is made clear especially by the comparison of the hydrolysis results of Example 5 (manganese dioxide catalyst without lanthanides), Example 6 (cerium-containing manganese dioxide catalyst) and Example 9 (lanthanum-containing manganese dioxide catalyst). While the conversion of 95.3% (Example 5) rises to 99.2% (Example 6) or 99.5% (Example 9) with approximately equal residence time, the selectivity with regard to undesired sulphoxide falls in the same series from 5.2% to 1.1% or 1.9%.

The best activation of the catalyst and reduction of sulphoxide formation in the hydrolysis reaction is achieved by preparing the catalyst by the process according to the invention described above in aqueous solution or suspension. Mixing and trituration of the manganese dioxide with the lanthanide salts in a more or less dry state leads only to limited success, as made clear by the comparison of Examples 5, 6 and 7.

By performing a process for catalytically hydrolysing thioether (S—R)— or thiol (S—H)-substituted, preferably S—R-substituted, carbonitriles of the general formula $R^1$—$CR^2R^3$—CN to the corresponding carboxamides with the aid of the above-described inventive catalyst, where $R^1$, $R^2$ and $R^3$ may be the same or different and are each hydrogen, at least one S—R- or S—H-substituted hydrocarbon radical and $R^3$ is optionally a hydroxyl radical, where the particular hydrocarbon radical $R^1$, $R^2$, $R^3$ is a linear or optionally branched $C_1$- to $C_{10}$-alkyl radical, a $C_6$- to $C_{10}$-aryl radical, an O-, N- and/or S-containing $C_4$- to $C_8$-heteroaryl radical or a $C_7$- to $C_{12}$-aralkyl radical, and the R radical is a linear or optionally branched $C_1$- to $C_4$-alkyl, $C_6$- to $C_{10}$-aryl radical, an O-, N- and/or S-containing $C_4$- to $C_8$-heteroaryl radical or a $C_7$- to $C_{12}$-aralkyl radical, the objects specified at the outset are achieved.

Preference is given to using S—R- or S—H-substituted, especially S—R-substituted, carbonitriles in which $R^1$, $R^2$, $R^3$, R are each $C_1$- to $C_4$-alkyl, phenyl, naphthyl, furyl, thienyl, imidazolyl, pyridyl, pyrimidyl or indolyl, benzyl or naphthylmethyl, in the case that $R^3$ is not a hydroxyl radical.

For example, in the case of 2-hydroxy-4-methylthio-butyronitrile, the process is notable for conversion rates of at least 96% up to 100%, depending on the precise selection of the conditions. Especially by virtue of sufficiently long reaction time, it is possible to achieve nitrile conversions of at least 99%, preferably $\geq$99.5% and up to 100%. At the same time, the selectivities for the undesired S-oxidation products of <2% of theory are obtained. Especially in the hydrolysis of carbonitriles containing thioether groups, selectivities of the undesired formation of sulphoxide products of significantly below 2% of theory, especially of preferably $\leq$1.1% of theory, most preferably up to $\leq$0.2% of theory, are enabled. This is very particularly advantageous with regard to the end product purity and with regard to the significantly reduced purification complexity.

When used once, the catalyst does not lose its activity. It is therefore possible without any problem to separate the catalyst, after the hydrolysis reaction has ended, from the reaction solution, and to use it again. The reaction can therefore be performed continuously and batchwise.

It has been found that, surprisingly, the oxidizing action of the catalyst on repeated use declines further without any deterioration in the performance for the hydrolysis reaction. Thus, the selectivity of undesired S-oxidation can be lowered down to <0.2%. The amount of catalyst used is not critical and has an influence only on the reaction rate.

It is particularly advantageous to use the catalyst in a continuous process. In this case, the nitrile can be hydrolysed by using catalyst-filled column reactors or else suspension reactors. It is also possible to select continuous stirred tank batteries or other embodiments known to those skilled in the art.

In this hydrolysis reaction, water is simultaneously solvent and reactant. The reaction is preferably performed in such a way that from 10 to 200 mol of water per mole of nitrile are used in the hydrolysis, more preferably from 20 to 100 mol of water. Especially in the case of hydrolysis of 2-hydroxy-4-methylthio-butyronitrile, the range between 20 and 100 mol of water per mole of nitrile is preferred. A larger amount of water is not harmful for the conversion and selectivity, but reduces the space-time yield.

Wherever it is more favorable for the solubility or miscibility of the reactants used and hence of the nitrile used, but especially in the case of a small amount of water, an inert organic solvent such as $C_1$- to $C_4$ alcohols, $C_3$- to $C_6$-ketones, preferably acetone, may be added as a solubilizer.

The temperatures at which the process according to the invention is performed can be varied within a wide range. Advantageously, the hydrolysis of the nitrile is, however, performed at temperatures of 10 to 90° C.; particular preference is given to a range from 20 to 50° C.

When cyanohydrins are used and higher temperatures of over 90° C. are employed, the reformation of aldehyde and hydrogen cyanide from the cyanohydrin is promoted and undesired by-products are formed. Therefore, a temperature range of from 20° C. to 50° C. is very particularly preferred here.

The process is preferably used to hydrolyse thioether (S—R)- or thiol (S—H)-substituted carbonitriles of the general formula $R^1$—$CR^2R^3$—CN defined above, in which $R^3$ is hydroxyl.

Among the corresponding cyanohydrin compounds $R^1$—$CR^2OH$—CN, very particular preference is given to those in which $R^1$, $R^2$ and R are represented by the $C_1$- to $C_4$-alkyl radicals as the alkyl radical, by phenyl or naphthyl as the aryl radical, by furyl, thienyl, imidazolyl, pyridyl, pyrimidyl or indolyl as the heteroaryl radical, and by benzyl or naphthylmethyl as the aralkyl radical.

In a quite outstanding manner, the process is suitable for hydrolysing 2-hydroxy-4-methylthiobutyronitrile to the corresponding 2-hydroxy-4-methylthiobutyramide.

The process can additionally also be used for the hydrolysis of non-sulphur-containing cyanohydrins.

Excellent yield and selectivities are achieved when acetone cyanohydrin is reacted under the above-specified conditions with an inventive manganese dioxide catalyst to give the isobutyramide, an important precursor for methacrylic acid compounds. The advantage here is in particular that it is possible with the same catalyst to hydrolyse S—R- and S—H-substituted nitriles and also unsubstituted nitriles. The process can thus be performed successively for sulphur-containing and for non-sulphur-containing nitriles in the same plant without a catalyst change, which advantageously increases the flexible usability of such plants.

The examples which follow are intended to illustrate the process without being restrictive.

Preparation of the Catalyst

Example 1

30 g of commercially available α-manganese dioxide of the HSA type from Erachem with a content of 1.6% potassium, a manganese content of 55%, a particle size range of 3.0 to 5.5 microns and a surface area of 230 $m^2/g$ together with 811 mg of cerium(III) phosphate in 300 ml of demineralized water were stirred at 60° C. for 24 hours. Thereafter, the solid was filtered off by means of a suction filter and washed with 1 l of demineralized water in 3 portions. The catalyst thus prepared was dried at 110° C. and 50 mbar for 20 hours. The specific surface area of the catalyst after drying was 239 $m^2/g$, the cerium content 0.97%.

Example 2

Example 1 was repeated, except that 1.15 g of cerium(IV) sulphate were used instead of cerium(III) phosphate. The specific surface area of the catalyst thus prepared after drying was 266 $m^2/g$.

Example 3

Example 1 was repeated, except that 1.4 g of lanthanum (III) nitrate hexahydrate were used instead of cerium(III) phosphate. The specific surface area of the catalyst thus prepared after drying was 283 $m^2/g$.

Example 4

A round-bottomed flask with stirrer and dropping funnel was initially charged with 14.2 g of potassium permanganate and 1.76 g of cerium(III) phosphate together with 550 ml of demineralized water and heated to 85° C. Within 2 minutes, a solution of 10.14 g of manganese(II) sulphate in 250 ml of demineralized water together with 4.1 g of concentrated sulphuric acid was added dropwise with vigorous stirring. The resulting black suspension was stirred at 85° C. for a further 6 hours. After cooling to 25° C., the solid was removed by suction filtering and washed with 2 l of water in 5 portions. The catalyst was dried at 110° C. and 50 mbar over 14 hours.

Catalytic Hydrolysis Reaction

Example 5: Comparative Example

Manganese Dioxide Catalyst without Lanthanides

In a round-bottomed flask with mechanical stirring, 2.0 g of unchanged α-manganese dioxide (HSA type from Erachem) and 120 g of demineralized water were heated to 40° C. in a waterbath, and 13.1 g of 2-hydroxy-4-methylthiobutyronitrile were added. After 2 hours, the conversion of the cyanohydrin was 95.3%. The HPLC analysis of the reaction solution showed a selectivity of 5.2% for the sulphoxide of 2-hydroxy-4-methyl-thiobutyramide.

Example 6

The experiment of Example 5 was repeated, except that the catalyst used was 2.0 g of the catalyst modified with cerium (III) phosphate from Example 1. After a reaction time of 2 hours at 40° C., 99.2% of the cyanohydrin had been converted. The selectivity for the sulphoxide was 1.1%.

Example 7

30 g of commercially available α-manganese dioxide (HSA type from Erachem) having a content of 1.6% potassium and a surface area of 230 $m^2/g$ were mixed with 811 mg of cerium(III) phosphate and triturated finely in a mortar. 2.0 g of this mixture were used as the catalyst in the hydrolysis of 13.1 g of 2-hydroxy-4-methylthiobutyronitrile with 120 g of water at a temperature of 40° C. After 2 hours, 96.8% of the cyanohydrin had been converted. The selectivity for the undesired sulphoxide was 4.2%.

Example 8

The experiment from Example 5 was repeated, except that the catalyst used was 2.0 g of the catalyst modified with cerium(IV) sulphate from Example 2. After a reaction time of 2 hours at 45° C., 99.6% of the cyanohydrin had been converted. The selectivity for the sulphoxide was 1.9%.

Example 9

The experiment from Example 5 was repeated, except that the catalyst used was 2.3 g of the catalyst modified with lanthanum nitrate from Example 3. After a reaction time of 2.5 hours at 35° C., 99.5% of the cyanohydrin had been converted. The selectivity for the sulphoxide was 1.9%.

Example 10

In an experimental series, the catalyst was recycled. To this end, in a round-bottomed flask with mechanical stirring, 2.0 g of the modified manganese dioxide according to Example 1 were heated with 120 g of demineralized water to 40° C. in a water bath, and 13.1 g of 2-hydroxy-4-methylthiobutyronitrile were added. After 2.5 hours, the conversion of the cyanohydrin was 99.8%. The selectivity for the sulphoxide was 1.1%. Thereafter, the catalyst was filtered off and used again in the hydrolysis reaction under the same conditions. This operation was performed a further 5 times. Thereafter, the cyanohydrin conversion was still 99.8%; the selectivity for the sulphoxide declined to 0.2%.

Example 11: Comparative Example

According to JP 09104665, Example 2

A glass column (diameter 1 cm, length 10 cm) was charged with 10 g of manganese dioxide catalyst (prepared according to JP 09104665, Example 1). A 10% by weight aqueous 2-hydroxy-4-methylbutyronitrile solution was pumped through the column in countercurrent at 10 g/h at 40° C. The effluent solution was analysed by means of HPLC. The run time was 100 hours from the start of the reaction. This gave a nitrile conversion of 96.1% of theory, an amide yield of 79.8% of theory (=83.0% selectivity) and a yield of 1.5% of theory of MHA amide sulphoxide (=1.6% selectivity). The amide yield reported in JP 09104665 Example 2 of at least 99.1% with 100% nitrile conversion could not be confirmed in any way. The yields decline even further when precisely 15% aqueous 2-hydroxy-4-methylbutyronitrile is used, since an oily second phase comprising predominantly nitrile separates out, which covers the catalyst and prevents uniform conversion.

In an analogously performed batch experiment, 2 g of manganese dioxide catalyst (prepared according to JP 09104665, Example 1) were reacted with 0.1 mol of 2-hydroxy-4-methylbutyronitrile as a 10% by weight aqueous solution at 40° C. within 3.5 hours. The amide yield was 81.6% of theory (=84.1% selectivity), the nitrile conversion 97.0% of theory. The yield of MHA amide sulphoxide was 4.0% of theory (=4.1% selectivity) based on nitrile used.

Further variations and modifications of the foregoing will be apparent to those skilled in the art and are intended to be encompassed by the claims appended hereto.

The invention claimed is:

1. An oxygen-containing manganese catalyst which contains at least 52% by weight of manganese of the formula:

$$MnMe_xM_yO_z,$$

where x is from 0.05 to 0.002, y is from 0.06 to 0.02 and z is from 1.7 to 2.0, Me is at least one element of the lanthanide group, M is an alkali metal and wherein additional water of hydration may be present.

2. Catalyst according to claim 1, wherein Me is cerium and/or lanthanum.

3. Catalyst according to claim 1, wherein M is potassium.

4. The catalyst according to claim 1 which has a specific surface area (BET) of 50 to 550 m²/g.

5. Catalyst according to claim 1, which has a specific surface area (BET) of 150 to 400 m²/g.

6. A process for preparing a catalyst of claim 1, comprising reacting an alkali metal-containing manganese dioxide in a reaction with at least one lanthanide salt in aqueous solution or suspension to obtain a solid, and removing the solid obtained, optionally washing and drying the solid.

7. Process according to claim 6, wherein the alkali metal-containing manganese dioxide is reacted with at least one lanthanide salt in aqueous solution or suspension to obtain a resulting solid, and the resulting solid with the composition $MnMe_xM_yO_z$ is obtained, removed, optionally washed and dried.

8. Process according to claim 6, further comprising before and/or during the reaction, alkali metal-containing manganese dioxide is prepared from alkali metal permanganate and manganese(II) sulphate in sulphuric acid solution.

9. Process according to claim 8, further comprising preparing alkali metal-containing manganese dioxide from approximately 2 molar equivalents of alkali metal permanganate and approximately 3 molar equivalents of manganese(II) sulphate.

10. Process according to claim 6, wherein the at least one lanthanide salt is an inorganic lanthanide salt or an organic lanthanide salt.

11. Process according to claim 10, wherein the at least one lanthanide salt is at least one selected from the group consisting of halides, nitrates, sulfates, and phosphates.

12. Process according to claim 10, wherein the at least one lanthanide salt is a carboxylic salt, a formate or an acetate.

13. Process according to claim 6 wherein the at least one lanthanide salt is a cerium and/or lanthanum salt.

14. Process according to claim 6, wherein the at least one lanthanide salt is a trivalent and/or tetravalent salt of cerium.

15. Process according to claim 6, wherein the manganese dioxide is present in the α-manganese dioxide crystal modification.

16. A Process for catalytic hydrolysis of carbonitriles of the general formula $R^1$—$CR^2R^3$—$CN$ to form the corresponding carboxamides, wherein $R^1$, $R^2$, and $R^3$ may be the same or different and are each hydrogen or at least one S—R- or S—H-substituted hydrocarbon radical which is a linear or branched $C_1$- to $C_{10}$-aryl radical; an O-, N- and/or S-containing $C_4$- to $C_8$-heteroaryl radical; or a $C_7$ to $C_{12}$-aralkyl radical; and wherein $R_3$ is optionally a hydroxyl radial, and the R radical is a linear or branched $C_1$ to $C_4$-alkyl radical; a $C_6$- to $C_{10}$-aryl radical; an O-, N- and/or S-containing $C_4$- to $C_8$-heteroaryl radical; or a $C_7$ to $C_{12}$-aralkyl radical, comprising carrying out the catalytic hydrolysis with the catalyst according to claim 1.

17. Process according to claim 16, wherein carbonitriles are used in which $R^1$, $R^2$, $R^3$, and R are each $C_1$- to $C_4$-alkyl, phenyl, naphthyl, furyl, thienyl, imidazolyl, pyridyl, pyrimidyl, indolyl, benzyl, or naphthylmethyl, and wherein $R^3$ is not a hydroxyl radical.

18. Process according to claim 16, wherein $R^3$ is hydroxyl.

19. Process according to claim 18, wherein $R^1$, $R^2$, and R are each $C_1$- to $C_4$-alkyl, phenyl, naphthyl, furyl, thienyl, imidazolyl, pyridyl, pyrimidyl, indolyl, benzyl, or naphthylmethyl.

20. Process according to claim 19, wherein 2-hydroxy-4-methylthiobutyronitrile is used hydrolyzed.

21. Process according to claim 16, further comprising when catalytic hydrolysis has ended, separating the catalyst from a reaction solution and using the catalyst again.

22. Process according to claim 16, wherein the process is continuous.

23. Process according to claim 22, wherein the carbonitrile is hydrolysed in column reactors or suspension reactors.

24. Process according to claim 16, wherein 10 to 200 moles of water are used per mole of carbonitrile in the hydrolysis.

25. Process according to claim 16, wherein the hydrolysis of the carbonitrile is performed in the presence of an inert organic solvent.

26. Process according to claim 16, wherein the hydrolysis of the carbonitrile is performed at temperatures of 10 to 90° C.

27. A process for catalytically hydrolysing acetone cyanohydrin to isobutyramide, wherein the hydrolysis is performed with the catalyst of claim 1.

28. A process for the hydrolysis of organic carbonitriles to the corresponding carboxylic acids, wherein the hydrolysis is carried out in the presence of the catalyst of claim 1.

29. The catalyst according to claim 1, wherein M is lithium, sodium, potassium, rubidium or cesium.

* * * * *

UNITED STATES PATENT AND TRADEMARK OFFICE
CERTIFICATE OF CORRECTION

PATENT NO. : 7,670,986 B2
APPLICATION NO. : 11/538898
DATED : March 2, 2010
INVENTOR(S) : Weigel et al.

It is certified that error appears in the above-identified patent and that said Letters Patent is hereby corrected as shown below:

In claim 16 lines 6 to 7, cancel the text "$C_1$- to $C_{10}$-aryl radical", and substitute the text --$C_1$- to $C_{10}$-alkyl radical; $C_6$- to $C_{10}$-aryl radical--;

line 8, cancel the text "$C_7$ to $C_{12}$-aralkyl", and substitute the text --$C_7$- to $C_{12}$-aralkyl--;

line 9, cancel the text "$R_3$ is optionally a hydroxyl radial", and substitute the text --$R^3$ is optionally a hydroxyl radical--;

line 10, cancel the text "$C_1$ to $C_4$-alkyl", and substitute the text --$C_1$- to $C_4$-alkyl--; and line 12, cancel the text "$C_7$ to $C_{12}$- aralkyl", and substitute the text --$C_7$- to $C_{12}$-aralkyl--.

Signed and Sealed this
Fifth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,670,986 B2  
APPLICATION NO. : 11/538898  
DATED : March 2, 2010  
INVENTOR(S) : Weigel et al.

Page 1 of 1

It is certified that error appears in the above-identified patent and that said Letters Patent is hereby corrected as shown below:

Column 10, lines 22-23 (Claim 16, lines 6-7)
cancel the text "$C_1$- to $C_{10}$-aryl radical", and substitute the text --$C_1$- to $C_{10}$-alkyl radical; $C_6$- to $C_{10}$-aryl radical--;

Column 10, line 24 (Claim 16, line 8)
cancel the text "$C_7$ to $C_{12}$-aralkyl", and substitute the text --$C_7$- to $C_{12}$-aralkyl--;

Column 10, line 25 (Claim 16, line 9)
cancel the text "$R_3$ is optionally a hydroxyl radial", and substitute the text --$R^3$ is optionally a hydroxyl radical--;

Column 10, line 26 (Claim 16, line 10)
cancel the text "$C_1$ to $C_4$-alkyl", and substitute the text --$C_1$- to $C_4$-alkyl--;

and

Column 10, line 28 (Claim 16, line 12)
cancel the text "$C_7$ to $C_{12}$- aralkyl", and substitute the text --$C_7$- to $C_{12}$-aralkyl--.

This certificate supersedes the Certificate of Correction issued July 5, 2011.

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,670,986 B2  
APPLICATION NO. : 11/538898  
DATED : March 2, 2010  
INVENTOR(S) : Weigel et al.

Page 1 of 1

It is certified that error appears in the above-identified patent and that said Letters Patent is hereby corrected as shown below:

Column 10, lines 21-22 (Claim 16, lines 6-7)
cancel the text "$C_1$- to $C_{10}$-aryl radical", and substitute the text --$C_1$- to $C_{10}$-alkyl radical; $C_6$- to $C_{10}$-aryl radical--;

Column 10, line 23 (Claim 16, line 8)
cancel the text "$C_7$ to $C_{12}$-aralkyl", and substitute the text --$C_7$- to $C_{12}$-aralkyl--;

Column 10, line 24 (Claim 16, line 9)
cancel the text "$R_3$ is optionally a hydroxyl radial", and substitute the text --$R^3$ is optionally a hydroxyl radical--;

Column 10, line 25 (Claim 16, line 10)
cancel the text "$C_1$ to $C_4$-alkyl", and substitute the text --$C_1$- to $C_4$-alkyl--;

and

Column 10, line 27 (Claim 16, line 12)
cancel the text "$C_7$ to $C_{12}$- aralkyl", and substitute the text --$C_7$- to $C_{12}$-aralkyl--.

This certificate supersedes the Certificates of Correction issued July 5, 2011 and August 16, 2011.

Signed and Sealed this
Twenty-eighth Day of February, 2012

David J. Kappos
*Director of the United States Patent and Trademark Office*